US008626529B1

(12) United States Patent
Pinsonneault

(10) Patent No.: US 8,626,529 B1
(45) Date of Patent: Jan. 7, 2014

(54) SYSTEMS AND METHODS FOR IDENTIFYING RISK EVALUATION AND MITIGATION STRATEGIES (REMS) COMPLIANCE

(75) Inventor: Roger Pinsonneault, Alpharetta, GA (US)

(73) Assignee: McKesson Financial Holdings, Hamilton (BM)

(*) Notice: Subject to any disclaimer, the term of this patent is extended or adjusted under 35 U.S.C. 154(b) by 116 days.

(21) Appl. No.: 13/298,806

(22) Filed: Nov. 17, 2011

(51) Int. Cl.
G06Q 50/00 (2012.01)
(52) U.S. Cl.
USPC .................................................. 705/2; 705/3
(58) Field of Classification Search
USPC ......................................................... 705/2, 3
See application file for complete search history.

(56) References Cited

U.S. PATENT DOCUMENTS

| 5,628,530 | A | 5/1997 | Thornton |
| 5,737,539 | A | 4/1998 | Edelson et al. |
| 5,845,255 | A | 12/1998 | Mayaud |
| 5,883,370 | A | 3/1999 | Walker et al. |
| 5,991,728 | A | 11/1999 | DeBusk et al. |
| 6,012,035 | A | 1/2000 | Freeman et al. |
| 6,021,392 | A | 2/2000 | Lester et al. |
| 6,112,182 | A | 8/2000 | Akers et al. |
| 6,529,801 | B1 | 3/2003 | Rosenblum |
| 6,581,204 | B2 | 6/2003 | DeBusk et al. |
| 6,757,898 | B1 | 6/2004 | Ilsen et al. |
| 6,766,218 | B2 | 7/2004 | Rosenblum |
| 6,769,228 | B1 | 8/2004 | Mahar |
| 7,155,397 | B2 | 12/2006 | Alexander et al. |
| 7,483,839 | B2 | 1/2009 | Mayaud |
| 7,519,540 | B2 | 4/2009 | Mayaud |
| 7,574,370 | B2 | 8/2009 | Mayaud |
| 7,606,723 | B2 | 10/2009 | Mayaud |
| 7,707,042 | B1 | 4/2010 | Konoske et al. |
| 7,765,107 | B2 | 7/2010 | Reardan et al. |

(Continued)

FOREIGN PATENT DOCUMENTS

| CA | 2482370 | 3/2006 |
| WO | 9503569 | 2/1995 |
| WO | 0039737 | 7/2000 |
| WO | 2007025295 | 3/2007 |

OTHER PUBLICATIONS

REMS: A new study for pharmacists?, U.S. Pharmacist, Jul. 20, 2011, Jesse C. Vivian, RPh, JD.*

(Continued)

Primary Examiner — Dilek B Cobanoglu
(74) Attorney, Agent, or Firm — Sutherland Asbill & Brennan LLP

(57) ABSTRACT

Systems and methods for identifying REMS compliance are provided. A service provider system that includes one or more computers may route one or more healthcare transactions submitted by a healthcare provider to one or more claims processor computers. One or more respective adjudicated replies received from the one or more claims processor computers for the one or more healthcare transactions may then be routed by the service provider system to the healthcare provider. Based at least in part upon information included in the routed healthcare claim transactions and adjudicated replies, an amount of a product dispensed by the healthcare provider may be determined by the service provider system. The determined dispensed amount may be compared to a purchased amount of the product. Based at least in part upon the comparison, a determination may be made as to whether a REMS condition associated with the product is satisfied.

20 Claims, 5 Drawing Sheets

(56) References Cited

U.S. PATENT DOCUMENTS

| | | | |
|---|---|---|---|
| 7,769,601 B1 | 8/2010 | Bleser et al. | |
| 7,797,171 B2 | 9/2010 | Reardan et al. | |
| 8,055,513 B1 | 11/2011 | Bleser et al. | |
| 8,099,339 B1 | 1/2012 | Pinsonneault et al. | |
| 8,478,605 B2 * | 7/2013 | Miller et al. | 705/2 |
| 2002/0002495 A1 | 1/2002 | Ullman | |
| 2002/0032582 A1 | 3/2002 | Feeney et al. | |
| 2002/0087583 A1 | 7/2002 | Morgan et al. | |
| 2002/0111832 A1 | 8/2002 | Judge | |
| 2002/0198831 A1 | 12/2002 | Patricelli et al. | |
| 2003/0009367 A1 | 1/2003 | Morrison | |
| 2003/0050799 A1 | 3/2003 | Jay et al. | |
| 2003/0149625 A1 | 8/2003 | Leonardi et al. | |
| 2003/0154163 A1 | 8/2003 | Phillips et al. | |
| 2003/0229540 A1 | 12/2003 | Algiene | |
| 2004/0039599 A1 | 2/2004 | Fralic | |
| 2004/0073457 A1 | 4/2004 | Kalies | |
| 2004/0078234 A1 | 4/2004 | Tallal, Jr. | |
| 2004/0117205 A1 | 6/2004 | Reardan et al. | |
| 2004/0117323 A1 | 6/2004 | Mindala | |
| 2004/0148198 A1 | 7/2004 | Kalies | |
| 2004/0230502 A1 | 11/2004 | Fiacco et al. | |
| 2004/0249745 A1 | 12/2004 | Baaren | |
| 2005/0015280 A1 | 1/2005 | Gabel et al. | |
| 2005/0060201 A1 | 3/2005 | Connely, III et al. | |
| 2005/0090425 A1 | 4/2005 | Reardan et al. | |
| 2005/0102169 A1 | 5/2005 | Wilson | |
| 2005/0149379 A1 | 7/2005 | Cyr et al. | |
| 2005/0154627 A1 | 7/2005 | Zuzek et al. | |
| 2005/0187793 A1 | 8/2005 | Myles | |
| 2005/0197862 A1 | 9/2005 | Paterson et al. | |
| 2005/0216309 A1 | 9/2005 | Reardan et al. | |
| 2005/0222874 A1 | 10/2005 | Reardan et al. | |
| 2005/0240473 A1 | 10/2005 | Ayers, Jr. et al. | |
| 2005/0288972 A1 | 12/2005 | Marvin et al. | |
| 2006/0020514 A1 | 1/2006 | Yered | |
| 2006/0026041 A1 | 2/2006 | Ullman | |
| 2006/0149784 A1 | 7/2006 | Tholl et al. | |
| 2006/0184391 A1 | 8/2006 | Barre et al. | |
| 2006/0259363 A1 | 11/2006 | Jhetam et al. | |
| 2007/0005402 A1 | 1/2007 | Kennedy et al. | |
| 2007/0050209 A1 | 3/2007 | Yered | |
| 2007/0136100 A1 | 6/2007 | Daugherty et al. | |
| 2007/0233525 A1 | 10/2007 | Boyle | |
| 2007/0233526 A1 | 10/2007 | Hoffman et al. | |
| 2007/0239493 A1 | 10/2007 | Sweetland et al. | |
| 2007/0260491 A1 * | 11/2007 | Palmer et al. | 705/3 |
| 2008/0065264 A1 | 3/2008 | Omura et al. | |
| 2009/0319293 A1 | 12/2009 | Lee et al. | |
| 2009/0326975 A1 | 12/2009 | Hardaway et al. | |
| 2010/0256984 A1 * | 10/2010 | Gold et al. | 705/2 |
| 2011/0016027 A1 | 1/2011 | Omura et al. | |
| 2011/0119085 A1 | 5/2011 | Reardan et al. | |
| 2011/0145018 A1 * | 6/2011 | Fotsch et al. | 705/3 |
| 2011/0302051 A1 | 12/2011 | Arbatli | |
| 2012/0041770 A1 | 2/2012 | Phillippe | |
| 2012/0047049 A1 | 2/2012 | Cadiz | |

OTHER PUBLICATIONS

Guidance Medication Guides—Distribution Requirements and Inclusion in Risk Evaluation and Mitigation Strategies (REMS), U.S. Department of Health and Human Services, Nov. 2011.*

New REMS Guidelines Raise Fears in Hospitals and Pharmacies, Stephen Barlas, Prescription Washington, Mar. 2010. vol. 35, No. 3.*

Google patents search, Aug. 26, 2013.*

Google Search, Aug. 26, 2013.*

Non-Final Office Action for U.S. Appl. No. 12/728,368 mailed Jan. 9, 2012.

Final Office Action for U.S. Appl. No. 12/728,368 mailed Apr. 23, 2012.

Sampson, R.J., Taking Control of Health Care Costs, Best's Review—Life Health Insurance Edition, Nov. 1983, pp. 64-66, vol. 84, Issue 7, USA.

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, pp. 128-132. vol. 63, Issue 1, USA.

Anonymous, TechRx Announces Successful Beta Deployment of T-Rex. PR Newswire. May 13, 2002.

Wermes, Mark K. Knowing claims switches can simplify your life. Drug Store News. p. 70. Nov. 23, 1992.

Sveum, Jerry. 340B: A new niche for pharmacy. Drug Topics. Oradell: Dec. 16, 2002. vol. 146, Iss. 23; p. 28.

Non-Final Office Action for U.S. Appl. No. 12/263,747 mailed Dec. 23, 2010.

Final Office Action for U.S. Appl. No. 12/263,747 mailed Jun. 9, 2011.

Notice of Allowance for U.S. Appl. 12/263,747 mailed Oct. 6, 2011.

Non-Final Office Action for U.S. Appl. No. 13/310,303 mailed Apr. 2, 2013.

Final Office Action for U.S. Appl. No. 13/310,303 mailed Jul. 31, 2013.

* cited by examiner

SYSTEMS AND METHODS FOR IDENTIFYING RISK EVALUATION AND MITIGATION STRATEGIES (REMS) COMPLIANCE

TECHNICAL FIELD

Aspects of the disclosure relate generally to healthcare transaction processing, and more particularly, to the processing of healthcare transactions to identify Risk Evaluation and Mitigation Strategies (REMS) compliance.

BACKGROUND

A wide variety of drugs and/or other products are dispensed by healthcare providers, such as pharmacies. The risk for fraud and abuse rises when the drugs being prescribed and dispensed are controlled substances or scheduled drugs. Scheduled drugs are those drugs classified in one of five schedules as determined by the Controlled Substances Act (CSA). The five schedules are categories separated by the abusive and/or addictive nature of the drug and include:

- Schedule I—a category of drugs not considered legitimate for medical use (e.g., heroin, lysergic acid diethylamide (LSD), etc.)
- Schedule II—a category of drugs considered to have a strong potential for abuse or addiction but that also have legitimate medical use (e.g., opium, morphine, etc.)
- Schedule III—a category of drugs that have less potential for abuse or addiction than Schedule I or II drugs and have a useful medical purpose (e.g., short-acting barbiturates and amphetamines, etc.)
- Schedule IV—a medically useful category of drugs that have less potential for abuse or addiction than those of Schedules I, II, and III (e.g., diazepam and chloral hydrate, etc.)
- Schedule V—a medically useful category of drugs that have less potential for abuse or addiction than those of Schedules I through IV (e.g., anti-diarrhea medication, etc.)

For such controlled substances as well as other prescription drugs, the Food and Drug Administration (FDA) is placing an increasing emphasis on Risk Minimization Action Plans (RiskMAPs) and Risk Evaluation and Mitigation Strategies (REMS) at the point of granting drug product approvals. A RiskMAP or a REMS program is typically a strategic safety program designed to meet specific goals and objectives in minimizing known risks of a product while preserving its benefits. Typically, a suitable RiskMAP or REMS program targets one or more safety-related health outcomes or goals and uses one or more tools to achieve those goals. Over time, the effectiveness of the tools is evaluated and the benefit-risk balance for the product is reassessed. Appropriate adjustments are then made to the risk minimization tools to further improve the benefit-risk balance.

A RiskMAP or REMS program may incorporate a plan for controlling and closely monitoring drug inventories and drug supply ordering. However, when it comes to drug inventory management, many pharmacies participate in an open distribution model in which a virtually unlimited number of wholesalers distribute products dispensed by any number of pharmacies. This open distribution model typically does not support product distribution and product dispensing controls and monitoring desirable for high risk drug products. Accordingly, there is an opportunity for improved systems and methods for identifying RiskMAP and/or REMS compliance. Additionally, there is an opportunity for improved systems and methods for detecting potential fraud in association with the distribution of drugs and/or other products.

BRIEF DESCRIPTION

Some or all of the above needs and/or problems, as well as additional needs and/or problems, may be addressed by certain embodiments of the disclosure. Embodiments of the disclosure may include systems and methods for identifying REMS compliance and/or potential fraud in association with the distribution of one or more products. In one embodiment, there is disclosed a method for identifying REMS compliance. A service provider system that includes one or more computers may route one or more healthcare transactions submitted by a healthcare provider to one or more claims processor computers. One or more respective adjudicated replies received from the one or more claims processor computers for the one or more healthcare transactions may then be routed by the service provider system to the healthcare provider. Based at least in part upon information included in the routed healthcare claim transactions and adjudicated replies, an amount of a product dispensed by the healthcare provider may be determined by the service provider system. The determined dispensed amount may be compared to a purchased amount of the product. Based at least in part upon the comparison, a determination may be made as to whether a REMS condition associated with the product is satisfied.

In another embodiment, there is disclosed a system for identifying and/or facilitating REMS. The system may include at least one memory and at least one processor. The at least one memory may be configured to store computer-executable instructions. The at least one processor may be configured to access the at least one memory and execute the computer-executable instructions to: direct the routing of one or more healthcare transactions submitted by a healthcare provider to one or more claims processor computers; direct the routing, to the healthcare provider, of one or more respective adjudicated replies received from the one or more claims processor computers for the one or more healthcare transactions; determine, based at least in part upon information included in the routed healthcare claim transactions and adjudicated replies, an amount of a product dispensed by the healthcare provider; compare the determined dispensed amount to a purchased amount of the product; and determine, based at least in part upon the comparison, whether a REMS condition associated with the product is satisfied.

Additional systems, methods, apparatus, features, and aspects may be realized through the techniques of various embodiments of the disclosure. Other embodiments and aspects of the disclosure are described in detail herein with reference to the description and to the drawings and are considered a part of the claimed invention.

DETAILED DESCRIPTION

Figure 1:
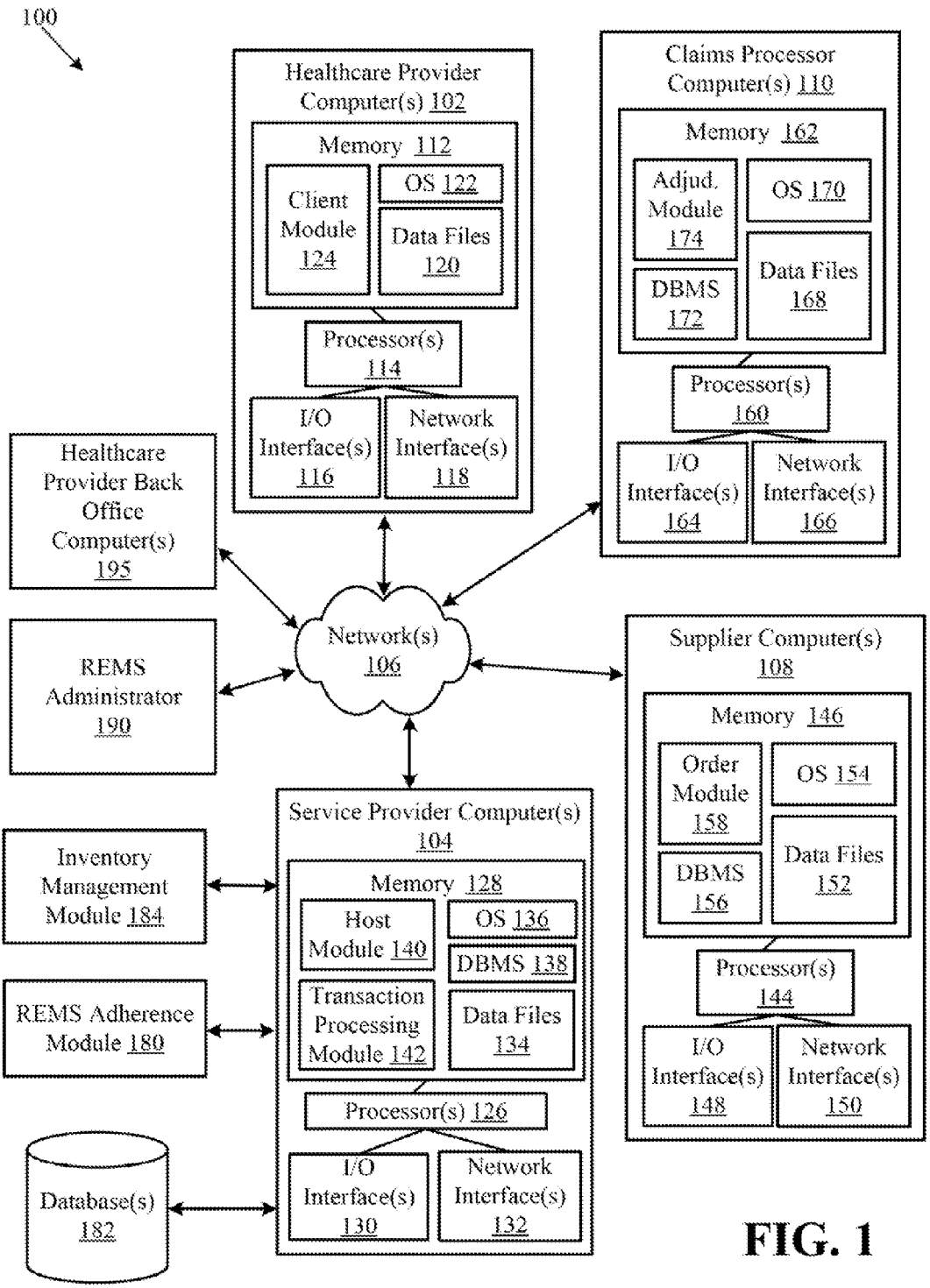
FIG. 1 is a block diagram of an example system for identifying and/or determining REMS compliance, according to an illustrative embodiment of the disclosure.

Embodiments of the disclosure now will be described more fully hereinafter with reference to the accompanying drawings, in which embodiments of the disclosure are shown. The invention may, however, be embodied in many different forms and should not be construed as limited to the embodiments set forth, herein; rather, these embodiments are provided so that this disclosure will be thorough and complete, and will fully convey the scope of the invention to those skilled in the art. Like numbers refer to like elements throughout.

Embodiments of the disclosure may include systems, methods, and apparatus for identifying REMS and/or Risk-MAP compliance. Additionally, embodiments of the disclosure may include systems, methods, and apparatus for identifying potential fraud and/or abuse in association with the distribution of one or more prescription products, such as controlled substances or drugs. Healthcare transactions may be evaluated as they are routed through a service provider system in order to determine or estimate an amount of a product dispensed by a healthcare provider. For example, an amount of a product dispensed during a given period of time may be determined from evaluating healthcare billing and/or claim transaction data. The estimated dispense or distribution amount may then be compared to purchase information for the product, such as invoice data obtained from one or more product manufacturers, suppliers, and/or distributors. In this regard, a determination may be made as to whether purchased amounts for the product correspond to amounts that are distributed and included in billing transactions. For example, an amount of the product that is likely distributed may be determined from purchase or ordering information, and the likely distributed amount may be compared to a dispensed amount determined from billing activity. The amounts may then be compared in order to evaluate any number of REMS conditions and/or to determine whether potential fraudulent activity exists.

In one example embodiment, a service provider system may be configured to route one or more healthcare transactions and associated adjudicated replies between healthcare providers (e.g., pharmacies, hospitals, etc.) and claims processors. For example, a healthcare transaction may be received from a healthcare provider computer, and the service provider system may route the healthcare transaction to a claims processor computer for adjudication. An adjudicated reply may then be received by the service provider system from the claims processor computer, and the adjudicated reply may be routed to the healthcare provider computer. A wide variety of suitable types of healthcare transactions may be routed as desired in various embodiments of the invention, such as healthcare claim transactions and claim reversal transactions.

During the routing of healthcare transactions, the service provider system and/or an associated REMS adherence module or system may be configured to collect respective dispense information associated with a wide variety of products, such as controlled substances, that are dispensed by various healthcare providers. In one example embodiment, a dispense amount for a product may be maintained over a desired period of time, such as a previous month, a previous three-month period, or some other period of time. Approved healthcare claim transactions may be evaluated or processed in order to increment the dispense amount Similarly, approved reversal transactions may be evaluated or processed in order to decrement the dispense amount. In this regard, a dispense amount for the product may be dynamically determined and/or maintained based upon billing transaction information.

Additionally, respective product ordering and/or purchase information may be obtained for the various healthcare providers. For example, order data, invoice data, shipment data, and/or receipt data may be obtained from any number of suitable sources, such as product manufacturers, product suppliers, product distributors, and/or healthcare provider back office computers or systems. In this regard, amounts of products that are likely distributed by a healthcare provider during the period of time may be determined. In other words, based upon an amount of a product that is ordered and/or supplied to a healthcare provider over time, a likely amount of the product that is distributed or dispensed by the healthcare provider may be determined.

Once a dispense amount associated with a product is determined from healthcare transaction information and a likely distribution amount is determined from ordering and/or purchase information, the two amounts may be evaluated in order to facilitate REMS compliance and/or to identify potentially fraudulent activity. A wide variety of suitable methods and/or techniques may be utilized to evaluate the dispense amount and the likely distribution amount. For example, the two amounts may be compared and, as desired, a difference and/or a deviation may be determined between the dispense amount and the likely distribution amount. As desired, the results of the comparison may be evaluated utilizing a wide variety of different threshold conditions and/or REMS parameters. For example, a determination may be made as to whether a deviation between the two amounts exceeds a threshold condition. In this regard, a determination may be made as to whether a REMS condition is satisfied and/or whether potentially fraudulent activity exists. For example, a determination may be made as to whether a healthcare provider is purchasing a greater amount of a product (e.g., a controlled substance) than the amount associated with healthcare transactions submitted by the healthcare provider.

In the event that a REMS condition is determined to not be satisfied or in the event that potentially fraudulent activity is identified, a wide variety of suitable control actions may be taken by the service provider system and/or the REMS adherence module. For example, a suitable alert message may be generated and communicated to any number of suitable recipients, such as a REMS administrator or a healthcare provider back office computer or system (e.g., a central office associated with a pharmacy chain, etc.). Additionally, as desired, a wide variety of REMS reports may be generated and distributed to designated recipients.

Additionally, in certain embodiments, the service provider system and/or an associated module may maintain inventory information on behalf of any number of healthcare providers. Based at least in part upon the processing and/or evaluation of healthcare transactions, inventory amounts for various products may be dynamically maintained. The inventory amounts may then be compared to one or more suitable threshold values, such as an ordering threshold value. In the event that a threshold value is satisfied, one or more messages associated with the ordering of additional product may be generated and communicated. For example, a message may be communicated to a healthcare provider indicating that additional product should be ordered. As another example, an ordering message may be communicated to a supplier on behalf of a healthcare provider.

System Overview

An example system 100 that facilitates the identification and/or determination of REMS compliance will now be described illustratively with respect to FIG. 1. As shown in FIG. 1, the system 100 may include at least one healthcare provider computer 102, at least one service provider computer 104, at least one supplier computer 108 (e.g., a drug wholesaler, manufacturer, distributor, corporate warehouse, or other drug product supplying entity), and/or at least one claims processor computer 110 (e.g., insurance programs, government funded programs, benefits managers, drug manufacturers, other vendors and/or business associates of healthcare service providers, government and/or non-government entities providing financial and/or administrative services, and the like). As desired, each of the healthcare provider computer 102, the service provider computer 104, the supplier computer 108, and/or the claims processor computer 110 may include one or more processing devices that may be configured for accessing and reading associated computer-readable media having stored thereon data and/or computer-executable instructions for implementing the various methods of the invention.

Additionally, in certain embodiments, the service provider computer 104 may include or otherwise be in communication with a REMS adherence module 180 or REMS adherence application, which may access and/or be in communication with one or more suitable data storage devices and/or databases 182. The REMS adherence module 180 may evaluate healthcare transactions associated with one or more healthcare providers and determine respective dispense amounts associated with any number of products, such as controlled substances. The REMS adherence module 180 may additionally collect and/or otherwise obtain purchasing information associated with the healthcare providers and products. The REMS adherence module 180 may compare the dispense amounts to product purchase amounts in order to determine whether billing transaction activity corresponds to purchasing activity. In this regard, the REMS adherence module 180 may determine whether one or more REMS conditions are satisfied. Additionally, as desired, the REMS adherence module 180 may determine whether potentially fraudulent activity has occurred.

In certain embodiments, the service provider computer 104 may include or otherwise be in communication with an inventory management module 184 or inventory management application, which may access and/or be in communication with the one or more databases 182. The inventory management module 184 may evaluate healthcare transactions associated with one or more healthcare providers and dynamically maintain and/or manage inventory amounts for various products (e.g., controlled substances, etc.) on behalf of the healthcare providers. When a determination is made that an inventory amount has satisfied a threshold value (e.g., the inventory amount has reached or fallen below a threshold value), a suitable message may be generated and transmitted to a healthcare provider computer 102 or directly to a supplier computer 108 as part of an order for additional inventory of the product. As a result, in certain embodiments, the service provider computer 104 may become a single point of product order. Additionally, increased product distribution and product dispensing controls may be provided over drug inventories (especially for high risk drug products) without overly limiting patient access or causing delay in the distribution of inventory.

Generally, network devices and systems, including one or more of the healthcare provider computer 102, the service provider computer 104, the supplier computer 108, and/or the claims processor computer 110 may include or otherwise be associated with suitable hardware and/or software for transmitting and receiving data, signals, and/or computer-executable instructions over one or more communications links or networks. As desired, these network devices and systems may also include any number of processors for processing data and executing computer-executable instructions, as well as other internal and peripheral components that are well-known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the healthcare provider computer 102, the service provider computer 104, the supplier computer 108, and the claims processor computer 110 may be in communication with each other via one or more networks, such as networks 106, which as described below can include one or more separate or shared private and public networks, including the Internet and/or a public switched telephone network. Each of these components—the healthcare provider computer 102, the service provider computer 104, the supplier computer 108, the claims processor computer 110, and the network 106—will now be discussed in further detail.

As desired, any number of healthcare provider computers may be associated with the system 100. Each healthcare provider computer 102 may be associated with a respective pharmacy or other healthcare provider (e.g., a physician's office, a hospital, etc). In certain embodiments, a pharmacy may be associated with a group of pharmacies, such as a pharmacy chain. A healthcare provider computer 102 may be any suitable processor-driven device that facilitates the processing of healthcare requests made by patients or consumers and the communication of information associated with healthcare transactions to the service provider computer 104. For example, the healthcare provider computer 102 may be a server computer, a mainframe computer, one or more networked computers, a desktop computer, a personal computer, a digital assistant, a personal digital assistant, a digital tablet, an Internet appliance, an application-specific circuit, a microcontroller, a minicomputer, or any other processor-based device. In certain embodiments, the healthcare provider computer 102 may be a suitable point of sale device associated with a pharmacy. The execution of the computer-implemented instructions by the healthcare provider computer 102 may form a special purpose computer or other particular machine operable to facilitate the processing of healthcare requests made by patients and the communication of information associated with healthcare transactions to a service provider computer 104. Additionally, in certain embodiments of the invention, the operations and/or control of the healthcare provider computer 102 may be distributed among several processing components.

In addition to having one or more processors 114, the healthcare provider computer 102 may include one or more memory devices 112, one or more input/output (I/O) interface(s) 116, and/or one or more network interface(s) 118. The memory devices 112 may be any suitable memory devices, for example, caches, read-only memory devices, random access memory devices, magnetic storage devices, removable storage devices, etc. The memory devices 112 may store data, executable instructions, and/or various program modules utilized by the healthcare provider computer 102, for example, data files 120, an operating system (OS) 122, and/or a client module 124. The data files 120 may include any suitable data that facilitates the receipt and/or processing of healthcare requests by the healthcare provider computer 102, the generation and/or processing of healthcare transactions that are communicated to the service provider computer 104, and/or the receipt and/or processing of responses to various transactions and/or messages associated with various transactions. For example, the data files 120 may include, but are not limited to, healthcare information associated with one or more patients, information associated with the service provider computer 104, information associated with one or more claims processors, and/or information associated with one or more healthcare transactions. The OS 122 may be a suitable software module that controls the general operation of the healthcare provider computer 102. The OS 122 may also facilitate the execution of other software modules by the one or more processors 114, for example, the client module 124. The OS 122 may be, but is not limited to, Microsoft Windows®, Apple OSX™, Linux, Unix, or a mainframe operating system. The client module 124 may be an Internet browser or other software, including a dedicated program, for interacting with the service provider computer 104. For example, a user, such as a pharmacist or other pharmacy employee, may utilize the client module 124 in preparing and providing a prescription claim request or a claim reversal request to the service provider computer 104 for delivery to the appropriate claims processor computer 110 for adjudication and/or coverage/benefits determination. The healthcare provider computer 102 may also utilize the client module 124 to retrieve or otherwise receive data, messages, or responses from the service provider computer 104 and/or other components of the system 100.

In one example operation, the healthcare provider computer 102 may receive information associated with a healthcare request for a patient. For example, information associated with a desired prescription may be received and/or identified. A healthcare transaction may be generated for the request, and information associated with the healthcare transaction may be communicated to the service provider computer 104. The healthcare provider computer 102 may then receive and process responses to the healthcare transaction, such as an adjudicated reply generated by the claims processor computer 110.

The one or more I/O interfaces 116 may facilitate communication between the healthcare provider computer 102 and one or more input/output devices, for example, one or more user interface devices, such as a display, keypad, control panel, touch screen display, remote control, microphone, barcode reader, scanner, etc., that facilitate user interaction with the healthcare provider computer 102. For example, the one or more I/O interfaces 116 may facilitate entry of information associated with a healthcare transaction by an employee of a pharmacy. The one or more network interfaces 118 may facilitate connection of the healthcare provider computer 102 to one or more suitable networks, for example, the networks 106 illustrated in FIG. 1. In this regard, the healthcare provider computer 102 may receive and/or communicate information to other network components of the system 100, such as the service provider computer 104.

With continued reference to FIG. 1, the service provider computer 104 may include, but is not limited to, any suitable processor-driven device configured for receiving, processing, and fulfilling requests from the healthcare provider computer 102, the supplier computer 108, and/or the claims processor computer 110 relating to prescriptions, pharmacy requests, benefits, healthcare transactions, therapeutic interchanges, and/or other activities. In certain embodiments, the service provider computer 104 may be a switch/router that routes healthcare transactions and/or other healthcare requests. For example, the service provider computer 104 may be configured to route billing requests, prescription claim requests, and/or reversal requests communicated from the healthcare provider computer 102 to a designated recipient, such as a claims processor (e.g., a pharmacy benefits manager (PBM), an insurer, a Medicare payer, another government payer, a claims clearinghouse, etc.). In certain embodiments, the service provider computer 104 may include a suitable host server, host module, or other software that facilitates the receipt of a healthcare transaction from a healthcare provider computer 102 and/or the receipt of transaction responses from a recipient. Any number of healthcare provider computers 102 and/or claims processor computers 110 may be in communication with the service provider computer 104 as desired in various embodiments of the invention.

The service provider computer 104 may include any number of special purpose computers or other particular machines, application-specific circuits, microcontrollers, personal computers, minicomputers, mainframe computers, servers, networked computers, and/or other processor-driven devices. In certain embodiments, the operations of the service provider computer 104 may be controlled by computer-executed or computer-implemented instructions that are executed by one or more processors associated with the service provider computer 104 to form a special purpose computer or other particular machine operable to facilitate receiving, routing, and/or processing of healthcare transactions. The one or more processors that control the operations of the service provider computer 104 may be incorporated into the service provider computer 104 and/or in communication with the service provider computer 104 via one or more suitable networks. In certain embodiments of the invention, the operations and/or control of the service provider computer 104 may be distributed among several processing components.

Similar to the healthcare provider computer 102, the service provider computer 104 may include one or more processors 126, one or more memory devices 128, one or more input/output (I/O) interface(s) 130, and/or one or more network interface(s) 132. The one or more memory devices 128 may be any suitable memory devices, for example, caches, read-only memory devices, random access memory devices, magnetic storage devices, removable memory devices, etc. The one or more memory devices 128 may store data, executable instructions, and/or various program modules utilized by the service provider computer 104, for example, data files 134, an operating system (OS) 136, the host module 140, a healthcare transaction processing module 142, and a database management system (DBMS) 138 to facilitate management of data files 134 and other data stored in the memory devices 128 and/or one or more databases 182. The OS 136 may be, but is not limited to, Microsoft Windows®, Apple OSX™, Linux, Unix, or a mainframe operating system. The OS 136 may be a suitable software module that controls the general operation of the service provider computer 104 and/or that facilitates the execution of other software modules.

The healthcare transaction processing module 142 may be operable to perform one or more pre-edits on a received healthcare transaction prior to routing or otherwise communicating the received healthcare transaction to a designated recipient computer. Additionally, the healthcare transaction processing module 142 may be operable to perform one or more post-edits on a reply received from a recipient computer for a healthcare transaction prior to routing the reply to the healthcare provider computer 102. A wide variety of different pre-edits and/or post-edits may be performed as desired in various embodiments of the invention. In certain embodiments, the REMS adherence module 180 may be incorporated into the healthcare transaction processing module 142 and/or in communication with the healthcare transaction processing module 142. For example, a REMS adherence service provided by the REMS adherence module 180 may be implemented as a post-edit.

According to an embodiment of the invention, the data files 134 may store healthcare transaction records associated with communications received from various healthcare provider computers 102 and/or various claims processor computers 110. The data files 134 may also store any number of suitable routing tables that facilitate determining the destination of communications received from a healthcare provider computer 102 or a claims processor computer 110. The host module 140 may receive, process, and respond to requests from the client module 124 of the healthcare provider computer 102, and may further receive, process, and respond to requests of the adjudication module 174 of the claims processor computer 110. The service provider computer 104 may include additional program modules for performing other processing methods described herein. Those of ordinary skill in the art will appreciate that the service provider computer 104 may include alternate and/or additional components, hardware or software without departing from example embodiments of the invention.

A REMS adherence module 180 or REMS adherence application may also be operative with the service provider computer 104. The REMS adherence module 180 may include computer-executable instructions for identifying REMS and/or RiskMAP compliance and/or identifying potential fraud and/or abuse in association with the distribution of one or more prescription products, such as controlled substances or drugs. In operation, the REMS adherence module 180 may evaluate healthcare transactions and/or adjudicated replies as they are routed through the service provider computer in order to determine or estimate an amount of a product dispensed by a healthcare provider. For example, an amount of a product dispensed during a given period of time (e.g., a previous month, a prior three-month period, etc.) may be determined from evaluating healthcare billing and/or claims transaction data. The estimated dispense or distribution amount may then be compared to purchase information for the product, such as invoice data obtained from one or more product manufacturers, suppliers, and/or distributors (and/or purchase information obtained from the inventory management module 184). In this regard, the REMS adherence module 180 may make a determination as to whether purchased amounts for the product correspond to amounts that are distributed and included in billing transactions. As a result, the REMS adherence module 180 may evaluate any number of REMS conditions and/or determine whether potential fraudulent activity exists.

In one example operation, the REMS adherence module 180 may receive information associated with a healthcare transaction from a service provider computer 102. For example, a healthcare transaction may received by the service provider computer 104 from a healthcare provider computer 102 and/or an adjudicated reply received from a claims processor computer 110 may be provided to the REMS adherence module 180 for evaluation. Information associated with a wide variety of suitable types of healthcare transactions may be received, such as healthcare claim transactions and claim reversal transactions. The REMS adherence module 180 may evaluate the received healthcare transaction information in order to track respective amounts of various healthcare products (e.g., controlled substances, etc.) that are dispensed by various healthcare providers and included in billing transaction information (e.g., submitted healthcare claims, etc.). For example, a dispense amount for a product may be maintained over a desired period of time, such as a previous month, a previous three month period, or some other period of time. Approved healthcare claim transactions may be evaluated or processed by the REMS adherence module 180 in order to increment the dispense amount. Similarly, approved reversal transactions may be evaluated or processed by the REMS adherence module 180 in order to decrement the dispense amount. In this regard, a dispense amount for the product may be dynamically determined and/or maintained based upon billing transaction information.

Additionally, the REMS adherence module 180 may obtain respective product ordering and/or purchasing information for the various healthcare providers. For example, order data, invoice data, shipment data, and/or receipt data may be obtained from any number of supplier computers 108, such as supplier computers associated with product manufacturers, product suppliers, and/or product distributors. As another example, ordering and/or purchasing information may be obtained from the inventory management module 184. In this regard, amounts of products that are likely distributed by a healthcare provider during the period of time may be determined. In other words, based upon an amount of a product that is ordered and/or supplied to a healthcare provider over time, a likely amount of the product that is distributed or dispensed by the healthcare provider may be determined by the REMS adherence module 180. The REMS adherence module 180 may then compare the dispense amount determined from healthcare transaction information to the likely distribution amount determined from ordering and/or purchasing information. In this regard, the REMS adherence module 180 may perform a wide variety of REMS compliance functions and/or the REMS adherence module 180 may identify potentially fraudulent activity.

A wide variety of suitable methods and/or techniques may be utilized to evaluate the dispense amount and the likely distribution amount. For example, the two amounts may be compared and, as desired, a difference and/or a deviation may be determined between the dispense amount and the likely distribution amount. As desired, the results of the comparison (e.g., a difference, a deviation, etc.) may be evaluated utilizing a wide variety of different threshold conditions and/or REMS parameters. For example, a determination may be made as to whether a deviation (e.g., a standard deviation, etc.) between the two amounts exceeds a threshold condition. In this regard, a determination may be made as to whether a REMS condition is satisfied and/or whether potentially fraudulent activity exists. For example, a determination may be made as to whether a healthcare provider is purchasing a greater amount of a product (e.g., a controlled substance) than the amount associated with healthcare transactions submitted by the healthcare provider.

As an alternative to maintaining a dispense amount for a product, the REMS adherence module 180, either by itself or in conjunction with the inventory management module 184, may maintain an inventory amount of the product at the healthcare provider. The inventory amount may be incremented or decremented based upon the evaluation of healthcare transactions. Additionally, as desired, a dispense amount over a desired period of time may be derived from the management of the inventory amount. In certain embodiments, as explained in greater detail below with reference to FIG. 4, a maintained inventory amount may also be evaluated based upon ordering and/or purchasing information. For example, if it is determined that an amount of a product that is ordered results in an inventory that exceeds an inventory threshold (e.g., a threshold associated with a maximum inventory allowed for the product), then a potentially fraudulent situation may be identified.

In the event that a REMS condition is determined to not be satisfied or in the event that potentially fraudulent activity is identified, a wide variety of suitable control actions may be taken by the REMS adherence module 180. For example, a suitable alert message may be generated and communicated to any number of suitable recipients, such as a REMS administrator 190 or a healthcare provider back office computer 195 (e.g., a central office associated with a pharmacy chain, etc.). Additionally, as desired, a wide variety of REMS reports may be generated and distributed to designated recipients.

Additionally, as desired, the REMS adherence module 180 may store or direct the storage of information associated with the processing of healthcare transactions in the databases or data storage devices 182. For example, the REMS adherence module 180 may store information associated with received healthcare transactions, received adjudicated replies, invoice and/or purchasing information, determined dispense amounts associated with various products and healthcare providers, determined likely distribution amounts determined for various products and healthcare providers, generated alerts, and/or information associated with other processing performed by the REMS adherence module 180. In certain embodiments, the stored information may be utilized for billing and/or reporting purposes. For example, the REMS adherence module 180 may utilize at least a portion of the stored information to bill pharmacies, pharmacy chains, and/or a REMS administrator for the services provided by the REMS adherence module 180.

The data storage devices 182 may be operable to store information associated with various rules, parameters, and/or edits that may be utilized by the REMS adherence module 180 and the inventory management module 184. For example, rules may be received from one or more other components of the system 100, such as the REMS administrator 190 and/or the healthcare provider back office computer 195. Additionally, the data storage devices 182 may be operable to store information associated with healthcare transactions, adjudicated replies, processing performed by the REMS adherence module 180, and/or processing performed by the inventory management module 184. In certain embodiments, the data storage devices 182 may additionally store billing information associated with the healthcare transactions and/or reports associated with the healthcare transactions and/or processing of the healthcare transactions. As desired, the data storage devices 182 may be accessible by the REMS adherence module 180, the inventory management module 184, and/or the service provider computer 104.

In certain embodiments, the REMS adherence module 180 and/or the service provider computer 104 may be operable to generate one or more reports associated with processed healthcare transactions. A wide variety of different types of reports may be generated as desired in various embodiments of the invention. Additionally, a wide variety of different information may be incorporated into generated reports, including but not limited to, a number of times the REMS adherence module 180 was invoked for a healthcare provider or chain of healthcare providers, information associated with the results of various processing performed by the REMS adherence module 180 (e.g., REMS compliance information, potentially fraudulent conditions, etc.), date information and/or date range information associated with processed healthcare transactions, financial information associated with the healthcare transactions, and/or billing information associated with the invocation of the REMS adherence module 180. Some reports may provide comparison information between purchased inventory and distributed or dispensed inventory accounted for by healthcare billing and/or claim transaction activity. These reports may be utilized to track certain drugs and/or other products, such as controlled substances susceptible to abuse to monitor for any cases of fraud, abuse, or error. As desired, these reports may be used by various third parties or government agencies, such as a REMS administrator 190, to monitor and police the disbursement of certain products that could be abused. Other reports may provide a manufacturer of a particular product information about how often a particular product is being prescribed or how often additional inventory of a particular product is ordered, etc. Reports may be sorted or formatted utilizing a wide variety of different criteria, parameters, and/or techniques. Additionally, the REMS adherence module 180 may communicate or direct the communication of generated reports to one or more other components of the system 100, for example, the REMS administrator 190 and/or the healthcare provider back office computer 195.

A wide variety of different techniques and/or software programs may be utilized to format a generated report. For example, a report may be formatted as a comma-separated-value (csv) file, as a spreadsheet file, as a word processor file, as a text file, etc. Additionally, a wide variety of different communication techniques may be utilized to communicate a report to the recipient, including but not limited to, email, short message service (SMS) messaging, other electronic communications, snail mail, etc. A report may be pushed to a recipient by the REMS adherence module 180 or other reporting module, or, alternatively pulled from the REMS adherence module 180 by a recipient submitting a request for one or more reports. Additionally, in certain embodiments, a report may be made available for download from an appropriate Web site or server, such as a Web site hosted by the service provider computer 104.

A few examples of the operations of the REMS adherence module 180 and/or the data storage devices 182 are described in greater detail below with reference to FIGS. 3-4. Additionally, although the REMS adherence module 180 is described as processing healthcare claim transactions and reversal transactions, as desired, the REMS adherence module 180 may also process information associated with cash transactions. For example, in the event that a patient purchases a controlled substance using cash, a healthcare provider may prepare and communicate a healthcare transaction associated with the cash transaction to the service provider computer 104 for evaluation by the REMS adherence module 180. In this regard, the REMS adherence module 180 may dynamically maintain a dispense amount for the healthcare provider even when patients purchase a product with cash. Indeed, in light of the risk associated with certain products, the healthcare providers may be required to communicate a healthcare transaction even if a purchase is made with cash.

As desired, an inventory management module 184 or inventory management application may also be operative with the service provider computer 104. Additionally, in certain embodiments, the service provider system and/or an associated module may maintain inventory information on behalf of any number of healthcare providers. Based at least in part upon the processing and/or evaluation of healthcare transactions, inventory amounts for various products may be dynamically maintained. The inventory amounts may then be compared to one or more suitable threshold values, such as an ordering threshold value. In the event that a threshold value is satisfied, one or more messages associated with the ordering of additional product may be generated and communicated. For example, a message may be communicated to a healthcare provider indicating that additional product should be ordered. As another example, an ordering message may be communicated to a supplier on behalf of a healthcare provider.

As desired, the inventory management module 184 may include a back-end analytic, editing, messaging, and reporting system for transactions between prescribing entities, healthcare providers, and wholesalers or other distributors. The inventory management module 184 may allow a healthcare provider (e.g., a pharmacy, etc.) to automatically order a particular product (or additional inventory of a product) via the submission of prescription claim transactions and/or other healthcare transactions to the service provider computer 104. The inventory management module 184 may reconcile healthcare transaction data (e.g., healthcare claim transactions, reversal transactions, etc.) to determine when a product order is desired. In one example operation, the inventory management module 184 may maintain a perpetual "on hand" inventory value for a particular product supply at a particular healthcare provider. For example, the inventory management module 184 may "net out" prescription claims and reversals on a daily basis. That is, an approved prescription claim transaction may decrement the "on hand" inventory value, while a claim reversal transaction may increment the "on hand" inventory value for a particular product supply at a particular healthcare provider. The inventory management module 184 may then compare the "netted out" activity for a particular product supply with a particular healthcare provider to a stored threshold value associated with the "on hand" inventory to determine if a product order transaction is desirable. In an example embodiment of the invention, the inventory management module 184 may initiate a product order transaction if the "on-hand" inventory is equal to (or less than) a threshold value.

When a product inventory has met the threshold value (e.g., equaling the threshold value or falling below the threshold value), the inventory management module 184 may create daily drug product order files for each wholesaler. In an example embodiment of the invention, the inventory management module 184 may create one consolidated product order file per supplier and send that product order file to the wholesaler. In an example embodiment, the product order file may be automatically created and sent to the supplier once the inventory level for a particular product has reached or gone beyond a preset threshold value (e.g., equaling the threshold value or falling below the threshold value), where the threshold value reflects an acceptable level of "on hand" inventory for a particular product where product ordering is desirable. In an alternative embodiment, a message may be generated and sent to the healthcare provider computer 102 contemporaneously with the delivery of the product order file to the supplier computer 108, or a message may be created and sent to the healthcare provider computer 102 for approval of the product ordering prior to the product order file being sent to the supplier computer 108.

With continued reference to the service provider computer 104, the one or more I/O interfaces 130 may facilitate communication between the service provider computer 104 and one or more input/output devices, for example, one or more user interface devices, such as a display, keypad, control panel, touch screen display, remote control, microphone, etc., that facilitate user interaction with the service provider computer 104. The one or more network interfaces 132 may facilitate connection of the service provider computer 104 to one or more suitable networks, for example, the networks 106 illustrated in FIG. 1. In this regard, the service provider computer 104 may communicate with other components of the system 100.

As desired, any number of supplier computers 108 may be utilized in association with various embodiments. Each supplier computer 108 may be associated with a manufacturer, distributor, and/or other supplier of healthcare products, such as various drugs and/or medications (e.g., controlled substances, etc.). With reference to FIG. 1, a supplier computer 108 may be any processor-driven device, such as, but not limited to, a server computer, a mainframe computer, one or more networked computers, a desktop computer, a personal computer, a laptop computer, a mobile computer, a handheld portable computer, a digital assistant, a personal digital assistant, a digital tablet, an Internet appliance, or any other processor-based device. Similar to other components of the system 100, the supplier computer 108 may include one or more processors 144, one or more memory devices 146, one or more input/output (I/O) interfaces 148, and/or one or more network interface(s) 150. The memory devices 146 may be any computer-readable medium, coupled to the processors 144, such as RAM, ROM, and/or a removable storage device for storing data files 152 and a database management system (DBMS) 156 to facilitate management of data files 152 and other data stored in the memory devices 146 and/or stored in separate databases. The memory devices 146 may also store various program modules, such as an operating system (OS) 154 and an order module 158. The OS 154 may be, but is not limited to, Microsoft Windows®, Apple OSX™, Linux, Unix, or a mainframe operating system. The order module 158 may receive, process, and respond to received order requests (e.g., order requests received from a healthcare provider, order requests received from the service provider computer 104 in association with the inventory management module, etc.) and/or requests for invoice and/or purchasing information associated with various healthcare providers.

In one example embodiment, the order module 158 may be configured to communicate ordering and/or purchasing information to the service provider computer 104 and/or the REMS adherence module 180. In certain embodiments, ordering and/or purchasing information for various products ordered by, purchased by, and/or shipped to various healthcare providers may be communicated in response to a received request for the information. For example, the order module 158 may respond to requests received from the service provider computer 104 and/or the REMS adherence module 180. In other embodiments, information may be pushed to a recipient by the order module 158. For example, information may be periodically provided to the service provider computer 104 and/or the REMS adherence module 180. As another example, information may be provided to the service provider computer 104 and/or the REMS adherence module 180 based upon the identification and/or occurrence of a predetermined condition (e.g., the processing of an order, etc.). A wide variety of different types of ordering and/or purchasing information may be communicated as desired in various embodiments, including but not limited to, invoice data, shipment data, purchase processing data, etc.

Additionally, as desired, the order module 158 may be configured to receive and process product orders, such as product orders received from a healthcare provider computer 102 or the inventory management module 184. The order module 158 may then facilitate the shipment or delivery of ordered products to a healthcare provider. During the processing of a product order, information associated with the order, shipment of product, and/or product billing may be communicated to the service provider computer 104 (or the REMS adherence module 180) and/or stored for subsequent communication and/or processing. In certain embodiments, the order module 158 may identify the products that are ordered, and the communication and/or storage of information may be based at least in part upon the identification. For example, information associated with controlled substances and/or other higher risk products may be communicated to a REMS adherence module 180 while information associated with other products is not communicated.

With continued reference to FIG. 1, the claims processor computer 110 may be any suitable processor-driven device that facilitates receiving, processing, and/or fulfilling healthcare transactions, such as healthcare claim requests and/or reversal requests, received from the service provider computer 104. For example, the claims processor computer 110 may be a processor-driven device associated with a pharmacy benefits manager (PBM), an insurer, a Medicare payer, another government payer, or a claims clearinghouse. As desired, the claims processor computer 110 may include any number of special purpose computers or other particular machines, application-specific circuits, microcontrollers, personal computers, minicomputers, mainframe computers, servers, and the like. In certain embodiments, the operations of the claims processor computer 110 may be controlled by computer-executed or computer-implemented instructions that are executed by one or more processors associated with the claims processor computer 110 to form a special purpose computer or other particular machine that is operable to facilitate the receipt, processing, and/or fulfillment of healthcare transaction requests received from the service provider computer 104. The one or more processors that control the operations of the claims processor computer 110 may be incorporated into the claims processor computer 110 and/or in communication with the claims processor computer 110 via one or more suitable networks. In certain embodiments of the invention, the operations and/or control of the claims processor computer 110 may be distributed among several processing components.

Similar to other components of the system 100, the claims processor computer 110 may include one or more processors 160, one or more memory devices 162, one or more input/output (I/O) interface(s) 164, and/or one or more network interface(s) 166. The one or more memory devices 162 may be any suitable memory devices, for example, caches, read-only memory devices, random access memory devices, magnetic storage devices, removable memory devices, etc. The one or more memory devices 162 may store data, executable instructions, and/or various program modules utilized by the claims processor computer 110, for example, data files 168, an operating system (OS) 170, a database management system (DBMS) 172, and an adjudication module 174. The data files 168 may include any suitable information that is utilized by the claims processor computer 110 to process healthcare transactions, for example, patient profiles, patient Medicare eligibility and/or insurance information, other information associated with a patient, information associated with a healthcare provider, information associated with previously processed healthcare transactions, etc. The OS 170 may be a suitable software module that controls the general operation of the claims processor computer 110. The OS 170 may also facilitate the execution of other software modules by the one or more processors 160, for example, the DBMS 172 and/or the adjudication module 174. The OS 170 may be, but is not limited to, Microsoft Windows®, Apple OSX™, Linux, Unix, or a mainframe operating system. The DBMS 172 may be a suitable software module that facilitates access and management of the data files 168 and/or one or more databases that are utilized to store information utilized by the claims processor computer 110 in various embodiments of the invention. The adjudication module 174 may initiate, receive, process, and/or respond to requests, such as healthcare transaction requests, from the host module 140 of the service provider computer 104. For example, a healthcare claim transaction may be received and adjudicated in order to determine benefits coverage. As another example, a reversal transaction may be received and adjudicated in order to reverse a previous healthcare claim transaction. The claims processor computer 110 may include additional program modules for performing other pre-processing or post-processing methods described herein. Those of ordinary skill in the art will appreciate that the claims processor computer 110 may include alternate and/or additional components, hardware or software without departing from example embodiments of the invention.

The one or more I/O interfaces 164 may facilitate communication between the claims processor computer 110 and one or more input/output devices, for example, one or more user interface devices, such as a display, keypad, control panel, touch screen display, remote control, microphone, etc. that facilitate user interaction with the claims processor computer 110. The one or more network interfaces 166 may facilitate connection of the claims processor computer 110 to one or more suitable networks, for example, the networks 106 illustrated in FIG. 1. In this regard, the claims processor computer 110 may receive healthcare transactions and/or other communications from the service provider computer 104, and the claims processor computer 110 may communicate information associated with processing claim transactions to the service provider.

With continued reference to FIG. 1, one or more REMS administrators 190 may be associated with the system 100. A REMS administrator 190 may be associated with a suitable entity, such as a governmental entity, that monitors and/or manages REMS and/or RiskMAP compliance and/or review. The REMS administrator 190 may include similar components as other devices included in the system 100, such as the healthcare provider computer 102 or the claims processor computer 110. For example, the REMS administrator 190 may be a processor-driven device that includes at least one memory, at least one processor, one or more I/O interfaces and/or one or more network interfaces. The REMS administrator 190 may further include software and/or computer-executable instructions that may be executed by the at least one processor to receive and process a wide variety of reports and/or alerts generated by the service provider computer 104, the REMS adherence module 180, and/or the inventory management module 184. Additionally, in certain embodiments, the REMS administrator 190 may be configured to provide REMS conditions and/or parameters, including various threshold parameters for identifying potentially fraudulent distribution of controlled substances, to the service provider computer 104 and/or the REMS adherence module 180.

The healthcare provider back office computer 195 may be one or more computers associated with a group of healthcare providers, such as a chain of pharmacies. The healthcare provider back office computer 195 may include similar components as other devices included in the system 100, such as the healthcare provider computer 102 or the claims processor computer 110. For example, the healthcare provider back office computer 195 may be a processor-driven device that includes at least one memory, at least one processor, one or more I/O interfaces and/or one or more network interfaces. The healthcare provider hack office computer 195 may further include software and/or computer-executable instructions that may be executed by the at least one processor to receive reports and/or billing information associated with the processing of healthcare claim transactions by the REMS adherence module 180 (and/or the inventory management module 184). For example, the healthcare provider back office computer 195 may be configured to receive reports associated with REMS compliance and/or alerts associated with potentially fraudulent activity. As another example, the healthcare provider back office computer 195 may be configured to receive information associated with the ordering of products and, as desired, the healthcare provider back office computer 195 may facilitate the ordering of products on behalf of individual healthcare providers. Additionally, as desired, the healthcare provider back office computer 195 may be operable or configured to provide a wide variety of ordering and/or purchasing information to the service provider computer 104 and/or the REMS adherence module 180. For example, in the event that the healthcare provider back office computer 195 facilitates the ordering of controlled substances and/or other products on behalf of pharmacies, the healthcare provider back office computer 195 may provide ordering and/or purchasing information to the service provider computer 104 and/or the REMS adherence module 180.

The networks 106 may include any number of telecommunication and/or data networks, whether public, private, or a combination thereof, including a local area network, a public switched telephone network, a wide area network, an intranet, the Internet, intermediate handheld data transfer devices, and/or any combination thereof and may be wired and/or wireless. For example, the networks 106 may include a public switched telephone network that facilitates telephone communication between various devices within the system 100.

Due to network connectivity, various methodologies as described herein may be practiced in the context of distributed computing environments. Although the service provider computer 104 is shown for simplicity as being in communication with the healthcare provider computer 102, the supplier computer 108, and the claims processor computer 110 via one intervening network 106, it is to be understood that any other network configuration is possible. For example, intervening network 106 may include a plurality of networks, each with devices such as gateways and routers for providing connectivity between or among networks 106. Instead of or in addition to a network 106, dedicated communication links may be used to connect the various devices in accordance with an example embodiment of the invention.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one embodiment, the service provider computer 104 (or other computer) may be implemented as a specialized processing machine that includes hardware and/or software for performing the methods described herein. In addition, at least a portion of the processor and/or processing capabilities of the service provider computer 104 and/or the REMS adherence module 180 may be implemented as part of the claims processor computer 110 or another component of the system 100. Accordingly, embodiments of the invention should not be construed as being limited to any particular operating environment, system architecture, or device configuration.

Operational Overview

Figure 2A:
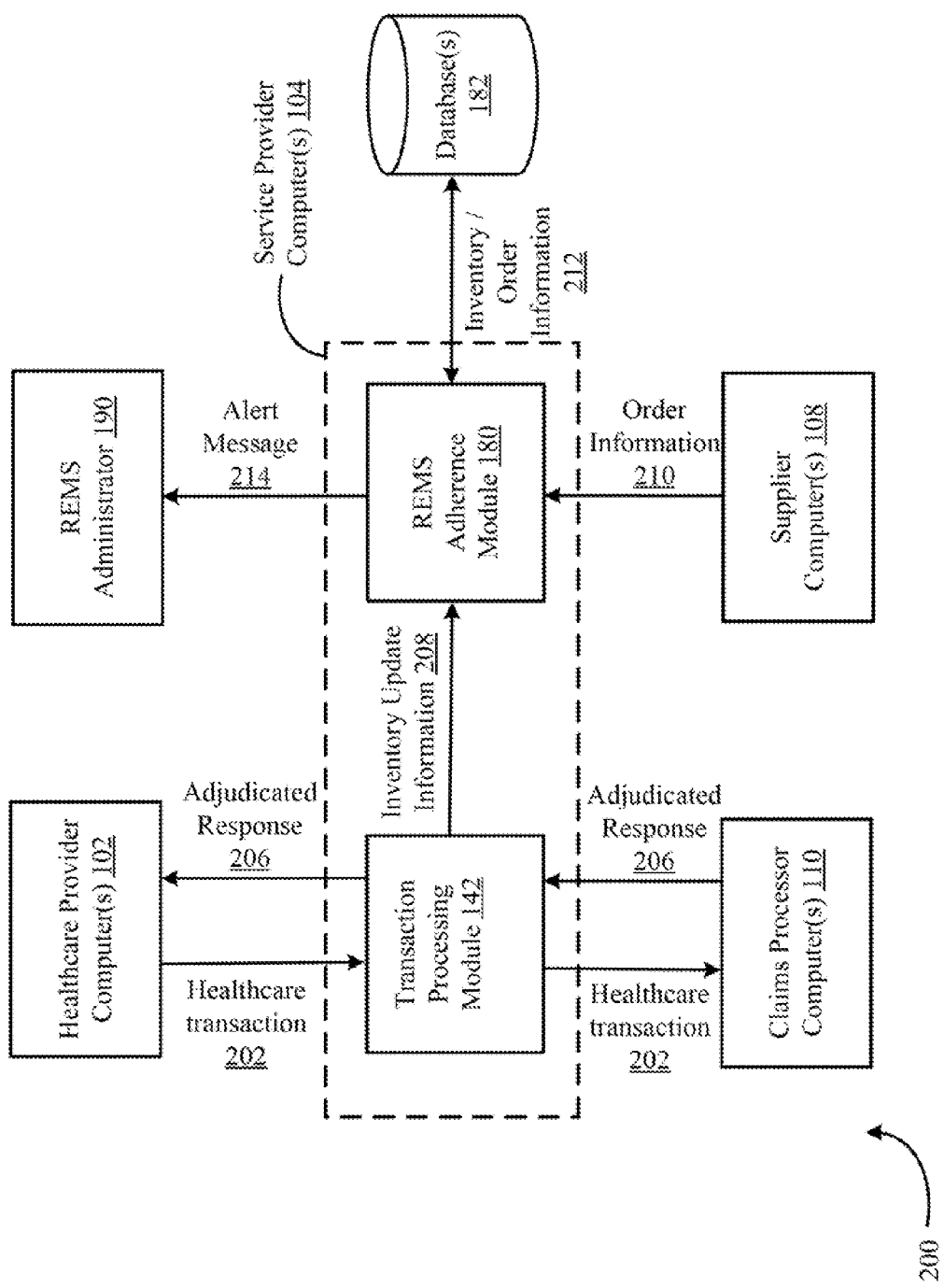
FIGS. 2A-2B are block diagrams of example data flows for evaluating healthcare transactions as the transactions are processed through a service provider, according to illustrative embodiments of the disclosure.

FIG. 2A is a block diagram of one example data flow 200 for evaluating healthcare transactions as the healthcare transactions are processed through a service provider, such as the service provider computer 104 illustrated in FIG. 1. The data flow 200 is one example data flow for processing healthcare transactions in order to determine a dispense amount for a product based upon billing and/or claim transaction activity. The data flow 200 additionally facilitates the collection of purchasing information associated with the product in order to determine a likely amount of the product that is distributed by the pharmacy. The two amounts may then be compared and/or otherwise evaluated in order to access REMS compliance and/or to identify potentially fraudulent situations.

Turning now to FIG. 2A, a healthcare request, such as a request for a prescription, may be received by a healthcare provider computer, such as the healthcare provider computer 102 illustrated in FIG. 1, from a patient. The healthcare request may be received in-person or electronically as desired in various embodiments of the invention. The healthcare provider computer 102 may receive and process the healthcare request to generate a healthcare transaction 202, such as a healthcare claim transaction. As another example, the healthcare provider computer 102 may generate a reversal transaction. The generated healthcare transaction 202 may be communicated by the healthcare provider computer 102 to the service provider computer 104. According to an example embodiment of the invention, the healthcare transaction 202 may be in accordance with a version of a National Council for Prescription Drug Programs (NCPDP) Telecommunication Standard, although other standards may be utilized as well. As desired, the healthcare transaction 202 may include a Banking Identification Number (BIN) and/or a Processor Control Number (PCN) for identifying a desired recipient for the healthcare transaction 202, such as the claims processor computer 110 illustrated in FIG. 1 In addition, the healthcare transaction 202 may also include a wide variety of healthcare information, such as information relating to the patient, payer, prescriber, pharmacy, and/or product. As an example, the healthcare transaction 202 received by the service provider computer 104 may include one or more of the following information:

Payer ID/Routing Information
    BIN Number (i.e. Banking Identification Number) and/or Processor Control Number (PCN) that designates a destination of the healthcare transaction 202
Patient Information
    Name (e.g., Patient Last Name, Patient First Name, etc.)
    Date of Birth of Patient
    Age of Patient
    Gender or Gender Code
    Patient Address (e.g., Street Address, Zip Code, etc.)
    Patient Contact Information (e.g., Patient Telephone Number, email address, etc.)
    Patient ID or other identifier
Insurance/Coverage Information
    Cardholder Name (e.g., Cardholder First Name, Cardholder Last Name)
    Cardholder ID and/or other identifier (e.g., person code)
    Group ID and/or Group Information
Healthcare Provider Information
    Prescriber Information
    Primary Care Provider ID or other identifier (e.g., National Provider Identifier (NPI) code)
    Primary Care Provider Name (e.g., Last Name, First Name)

Prescriber ID or other identifier (e.g., NPI code, DEA number)
Prescriber Name (e.g., Last Name, First Name)
Prescriber Contact Information (e.g., Telephone Number, Email Address, Fax Number, etc.)
Pharmacy or other Healthcare Provider Information (e.g., store name, chain identifier, etc.)
Pharmacy or other Healthcare Provider ID (e.g., NPI code)
Claim Information
Drug or product information (e.g., National Drug Code (NDC))
Prescription/Service Reference Number
Date Prescription Written
Quantity Dispensed
Number of Days Supply
Diagnosis/Condition
Pricing information for the drug or product (e.g., network price, Usual & Customary price)
One or more NCPDP Message Fields
Date of Service.

With continued reference to FIG. 2A, the service provider computer 104 may receive the healthcare transaction 202 from the healthcare provider computer 102, and the service provider computer 104 may process the received healthcare transaction 202. As desired, the service provider computer 104 and/or an associated transaction processing module 142, may perform one or more pre-edits on the healthcare transaction 202. The pre-edits may verify, add, and/or edit information included in the healthcare transaction 202 prior to the healthcare transaction 202 being communicated to an appropriate recipient. According to an example embodiment, the service provider computer 104 and/or the transaction processing module 142 may utilize at least a portion of the information included in the healthcare transaction 202, such as a BIN/PCN, to identify the claims processor computer 110 as an appropriate recipient for routing. The service provider computer 104 may also include a routing table, perhaps stored in memory, for determining a recipient. Once identified, the healthcare transaction 202 or a copy thereof may be routed to the claims processor computer 110.

The claims processor computer 110 may receive and adjudicate or otherwise process the healthcare transaction 202. For example, the recipient may determine benefits coverage for a healthcare claim transaction according to an adjudication process associated with eligibility, pricing, and/or utilization review. As another example, the claims processor computer 110 may process a received reversal transaction in order to facilitate a reversal of a previously approved claim transaction. Following the adjudication, the claims processor computer 110 may transmit an adjudicated response 206 or adjudicated reply for the healthcare transaction 202 to the service provider computer 104. The service provider computer 104 may receive the adjudicated response 206 from the claims processor computer 110 and provide the adjudicated response 206 to the transaction processing module 142. As desired, the transaction processing module 142 may perform any number of post-edits on the adjudicated response 206. The adjudicated response 206 or a copy thereof may then be routed or otherwise communicated to the healthcare provider computer 102.

Based at least in part upon the processing of the healthcare transaction 202 and/or the adjudicated response 206 by the transaction processing module 142, the transaction processing module 142 may communicate inventory update information 208 and/or other information to the REMS adherence module 180. For example, in the event that the healthcare transaction 202 is a healthcare claim transaction that has been approved (as indicated by the adjudicated response 206), then dispense increment information or inventory decrement information may be communicated to the REMS adherence module 180. As one example, a product associated with the healthcare transaction 202 and an amount of the product may be determined and utilized to communicate dispense increment information. As another example, in the event that the healthcare transaction 202 is a reversal transaction that has been approved (as indicated by the adjudicated response 206), then dispense decrement information or inventory increment information may be communicated to the REMS adherence module 180. In this regard, a dispensed amount of the product may be dynamically maintained by the REMS adherence module 180.

As an alternative to communicating increment and/or decrement information to the REMS adherence module 180, in certain embodiments, the transaction processing module 142 may communicate information extracted from the healthcare transaction 202 and/or adjudicated response 206 to the REMS adherence module 180. For example, product identifying information (e.g., an NDC code, etc.) and dispense amount information may be provided to the REMS adherence module 180. The REMS adherence module 180 may then process the information in order to determine increments and/or decrements of a total dispensed amount by the healthcare provider and/or a product inventory. In yet other embodiments, a copy of the healthcare transaction 202 and/or the adjudicated response 206 may be communicated to the REMS adherence module 180 for processing in order to maintain and/or determine a total dispensed amount of a product associated with the healthcare transaction 202. Regardless of the information communicated to the REMS adherence module 180, in certain embodiments, the REMS adherence module 180 may be selectively invoked based upon an identification of a product associated with the healthcare transaction 202. For example, a product identifier (e.g., an NDC code, etc.) may be compared to a list of product identifiers associated with the invocation of the REMS adherence module 180 (e.g., a list of controlled substances, etc.), and the REMS adherence module 180 may be selectively invoked based upon a determination of whether a product identifier is included in the list.

The REMS adherence module 180 may receive information from the transaction processing module 142, and the REMS adherence module 180 may process at least a portion of the received information in order to determine and/or maintain a dispensed amount (or inventory) for a product provided by a healthcare provider associated with the healthcare transaction 202. In certain embodiments, the dispensed amount may be determined and/or maintained over any desired period of time. For example, the dispensed amount of a product may be determined and/or maintained over a previous month, a previous three months, and/or any other time period. In this regard, dispense information for a product and a healthcare provider may be dynamically maintained by the REMS adherence module 180 based upon an analysis of billing and/or claim transaction information for the healthcare provider.

Additionally, the REMS adherence module 180 may obtain order and/or purchase information 210 associated with the product. As desired, order and/or purchase information 210 may be obtained from a wide variety of different sources. For example, order and/or purchase information 210 may be obtained from a supplier computer 108 associated with a manufacturer, distributor, and/or supplier of the product. As another example, order and/or purchase information 210 may be obtained from an inventory management module, such as the inventory management module 184 illustrated in FIG. 1. A wide variety of different types of order and/or purchase information 210 may be obtained as desired, including but not limited to, invoice data, shipment data, and/or billing data. Based at least in part upon an analysis and/or evaluation of the obtained order and/or purchase information 210, the REMS adherence module 180 may determine or estimate a distribution amount (or available inventory) for the product. In other words, based upon an evaluation of the amount of a product ordered and/or supplied to a healthcare provider, an estimate of the amount of product distributed or dispensed by the healthcare provider may be determined. As desired, the distribution amount may be determined over any desired period of time, such as the same period of time utilized to evaluate healthcare transaction information.

As desired in various embodiments, the REMS adherence module 180 may compare a determined or maintained dispense amount (e.g., an amount determined from healthcare transaction data) to a determined or estimated distribution amount (e.g., an amount determined or estimated from ordering information). As desired, a determination may be made as to whether the two amounts correspond to one another. In this regard, a determination may be made as to whether a healthcare provider is ordering a greater amount of a product (e.g., a controlled substance) than the amount of the product reported by healthcare transactions. For example, a difference and/or deviation between the two amounts may be determined and compared to one or more threshold values and/or REMS conditions in order to determine whether a correspondence exists. In the event that a determination is made that the two amounts do not correspond to one another, the REMS adherence module 180 may identify a potentially fraudulent situation. As desired, a suitable alert message 214 associated with the potentially fraudulent situation may be generated and communicated to one or more suitable recipients, such as a REMS administrator 190 and/or a healthcare provider back office computer 195.

According to an aspect of the invention, the REMS adherence module 180 may store information 212 associated with the processed healthcare transaction 202 and/or ordering information for a wide variety of reporting and/or billing purposes. A wide variety of information 212 may be stored as desired in various embodiments, for example, a copy of the healthcare transaction 202, information extracted from the healthcare transaction 202, information associated with the processing of the REMS adherence module 180, a dispensed amount, inventory information, ordering and/or purchase information, a determined distribution amount, REMS compliance information, correspondence information associated with the dispensed amount and distribution amount, information associated with identified fraudulent situations, and/or generated alert messages 214. In certain embodiments, information associated with the invocation of the REMS adherence module 180 may be communicated to an appropriate billing system associated with the service provider computer 104 in order to facilitate billing customers, such as healthcare providers, for the services provided by the REMS adherence module 180. Alternatively, the REMS adherence module 180 may alter a billing code or other field of the healthcare transaction 202 to a value indicating that the healthcare transaction 202 has been evaluated or processed by the REMS adherence module 180. The altered billing code may be recognized during subsequent or further processing of the healthcare transaction 202, such as further processing by the service provider computer 104, in order to facilitate billing.

According to another aspect of the invention, the REMS adherence module 180 or a reporting system associated with the REMS adherence module 180 and/or service provider computer 104 may utilize at least a portion of stored information 212 to generate one or more reports that include information associated with the processing of the REMS adherence module 180. The generation of reports is discussed in greater detail above with respect to FIG. 1. As desired, generated reports may be communicated to customers of the service provider and/or to other systems, for example, the REMS administrator 190 and/or the healthcare provider back office computer 195. A wide variety of suitable communications techniques, for example, electronic mail, short message service (SMS) messaging, other electronic communications, snail mail, etc., may be utilized as desired to communicate generated reports to one or more recipients.

In the example embodiment of FIG. 2A, the transaction processing module 142 and the REMS adherence module 180 are incorporated into the service provider computer 104. In alternative embodiments, one or more of these modules may be separate and distinct from the service provider computer 104 and in communication with the service provider computer 104. Additionally, as desired, the transaction processing module 142 and the REMS adherence module 180 may be in communication with one another either electronically, or in an alternative embodiment, data may be provided between the two modules manually. In yet another alternative embodiment, functionality described for the transaction processing module 142 and the REMS adherence module 180 may be combined into a single module.

Figure 2B:
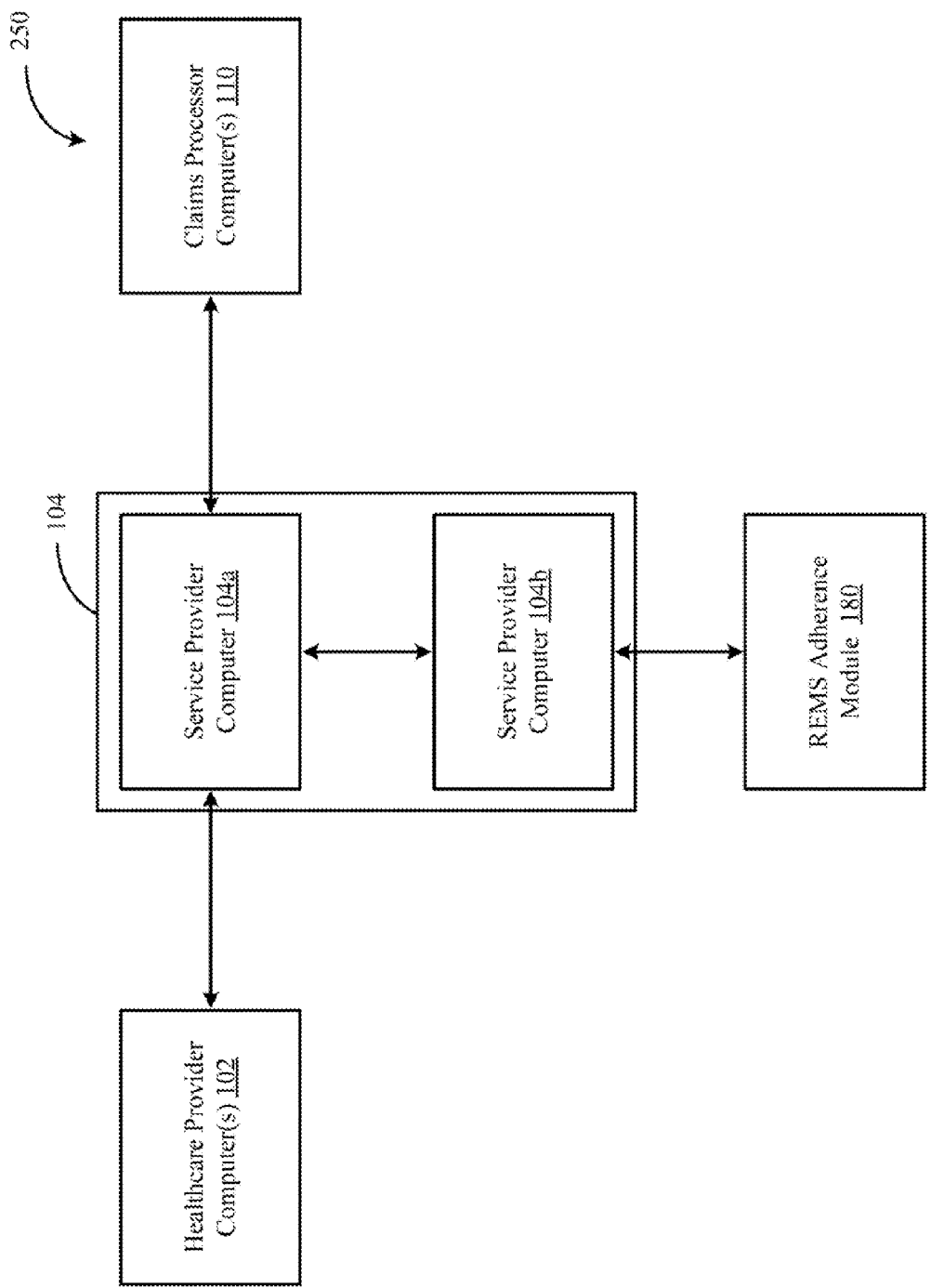

It will be appreciated that variations of the data flow 200 illustrated in FIG. 2A may be utilized in accordance with various embodiments of the invention. For example, as shown in FIG. 2B, the service provider computer 104 may be comprised of two or more distinct service provider computers 104a and 104b that are in communication with each other. Service provider computer 104a may be operative with one or more healthcare provider computers and claims processor computers, such as the healthcare provider computer 102 and/or the claims processor computer 110 illustrated in FIG. 1. However, service provider computer 104b may have a data processing arrangement with service provider computer 104a. Under the data processing agreement, the service provider computer 104a may be permitted to utilize or offer services of the service provider computer 104b, including those of the REMS adherence module 180. For example, a first service provider may communicate healthcare transactions to a second service provider for processing.

As described herein, healthcare transactions may be examined as they are routed to or through a service provider computer 104. In this regard, a REMS adherence service may be provided as various transactions are routed to or through the service provider computer 104. FIG. 3 is a flow diagram of an example method 300 for processing a healthcare transaction, according to an illustrative embodiment of the disclosure. The method 300 may be performed by a suitable service provider computer and/or an associated REMS adherence module, such as the service provider computer 104 and the REMS adherence module 180 illustrated in FIG. 1. The method 300 may begin at block 305.

At block 305, a healthcare transaction may be received from a healthcare provider computer, such as the healthcare provider computer 102 shown in FIG. 1. For example, a healthcare claim transaction or a reversal transaction may be received. One or more pre-edits and/or evaluations may be performed on the received healthcare transaction as desired in various embodiments of the invention. For example, one or more pre-edits may be performed by a transaction processing module associated with the service provider computer 104, such as the transaction processing module 142 shown in FIG. 1. At block 310, the healthcare transaction may be routed or otherwise communicated to a suitable recipient, such as the claims processor computer 110 illustrated in FIG. 1, for adjudication. Additionally, at block 315, an adjudicated response for the healthcare transaction may then be received from the claims processor computer 110 and, as desired, routed or otherwise communicated to the healthcare provider computer 102.

At block 320, a determination may be made as to whether a REMS adherence service or REMS adherence edit has been enabled and/or activated for a healthcare provider that submitted the healthcare transaction, for a group or chain to which the healthcare provider belongs, and/or for a REMS adjudicator. For example, processing parameters for the healthcare provider, group of healthcare providers (e.g., pharmacy chain), and/or REMS adjudicator may be analyzed in order to determine whether a REMS adherence service has been enabled. If it is determined at block 320 that a REMS adherence service has not been enabled, then operations may end.

If, however, it is determined at block 320 that a REMS adherence service has been enabled, then operations may continue at block 325. At block 325, the healthcare transaction may be processed by the REMS adherence module 180 or REMS adherence application. The REMS adherence module 180 may evaluate the healthcare transaction in order to dynamically maintain a dispense amount for a product associated with the healthcare transaction. Additionally, the REMS adherence module 180 may obtain ordering and/or purchase information for the healthcare provider and determine a likely distribution amount associated with the product. The REMS adherence module 180 may compare the dispense amount and the distribution amount in order to determine whether the healthcare provider is complying with one or more REMS conditions and/or whether potentially fraudulent activity has occurred. \One example of the operations that may be performed by the REMS adherence module 180 in order to evaluate or process the healthcare transaction is described in greater detail below with reference to FIG. 4.

At block 330, a determination may be made as to whether an alert has been generated by the REMS adherence module 180. For example, a determination may be made as to whether an alert associated with potentially fraudulent activity has been generated. If it is determined at block 330 that an alert has not been generated, then operations may continue at block 340 described in greater detail below. If, however, it is determined at block 330 that an alert has been generated, then operations may continue at block 335. At block 335, a suitable alert message associated with the generated alert may be communicated to one or more appropriate recipients, such as a REMS administrator 190 or a healthcare provider back office computer 195. Operations may then continue at block 340.

At block 340, which may be optional in certain embodiments of the invention, information associated with the healthcare transaction and/or the invocation of the REMS adherence module 180 may be stored and/or communicated for billing and/or reporting purposes. As explained in greater detail above, a wide variety of information may be stored in various embodiments of the invention. As desired in certain embodiments, billing information may be communicated to a suitable billing system associated with the service provider. In other embodiments, billing information may be stored for subsequent access by a billing system or for subsequent access by another component of the service provider for communication to the billing system. Billing information may be utilized by the billing system in order to charge customers of the service provider for the REMS adherence service provided by the REMS adherence module 180. A wide variety of different types of billing information may be stored and/or communicated as desired in various embodiments of the invention, for example, an identifier associated with the invocation of the REMS adherence module 180 or a billing code (e.g., a unique billing code) associated with the invocation of the REMS adherence module 180. As an alternative to storing or communicating billing information, the REMS adherence module 180 may set a billing code for the healthcare transaction to a unique billing code associated with the provided REMS adherence service. The unique billing code may be identified or recognized during subsequent processing of the healthcare transaction by either the billing system or a component of the service provider computer 104. The identified billing code may then be utilized by the billing system in the generation of bills for customers of the service provider.

At block 345, which may be optional in certain embodiments of the invention, one or more reports may be generated utilizing at least a portion of the stored information. For example, reports may be generated by the REMS adherence module 180, the service provider computer 104, and/or a separate reporting module. As described in greater detail above, a wide variety of different information may be included in a generated report. Additionally, generated reports may be formatted and/or sorted utilizing a wide variety of different parameters and/or criteria, such as identifiers for healthcare providers, identifiers for products and/or services associated with healthcare transactions, dates of service, etc. As desired, generated reports may be communicated to one or more recipients, such as the REMS administrator 190 and/or a healthcare provider back office computer 195.

The method 300 may end following either block 320 or block 345.

Figure 3:
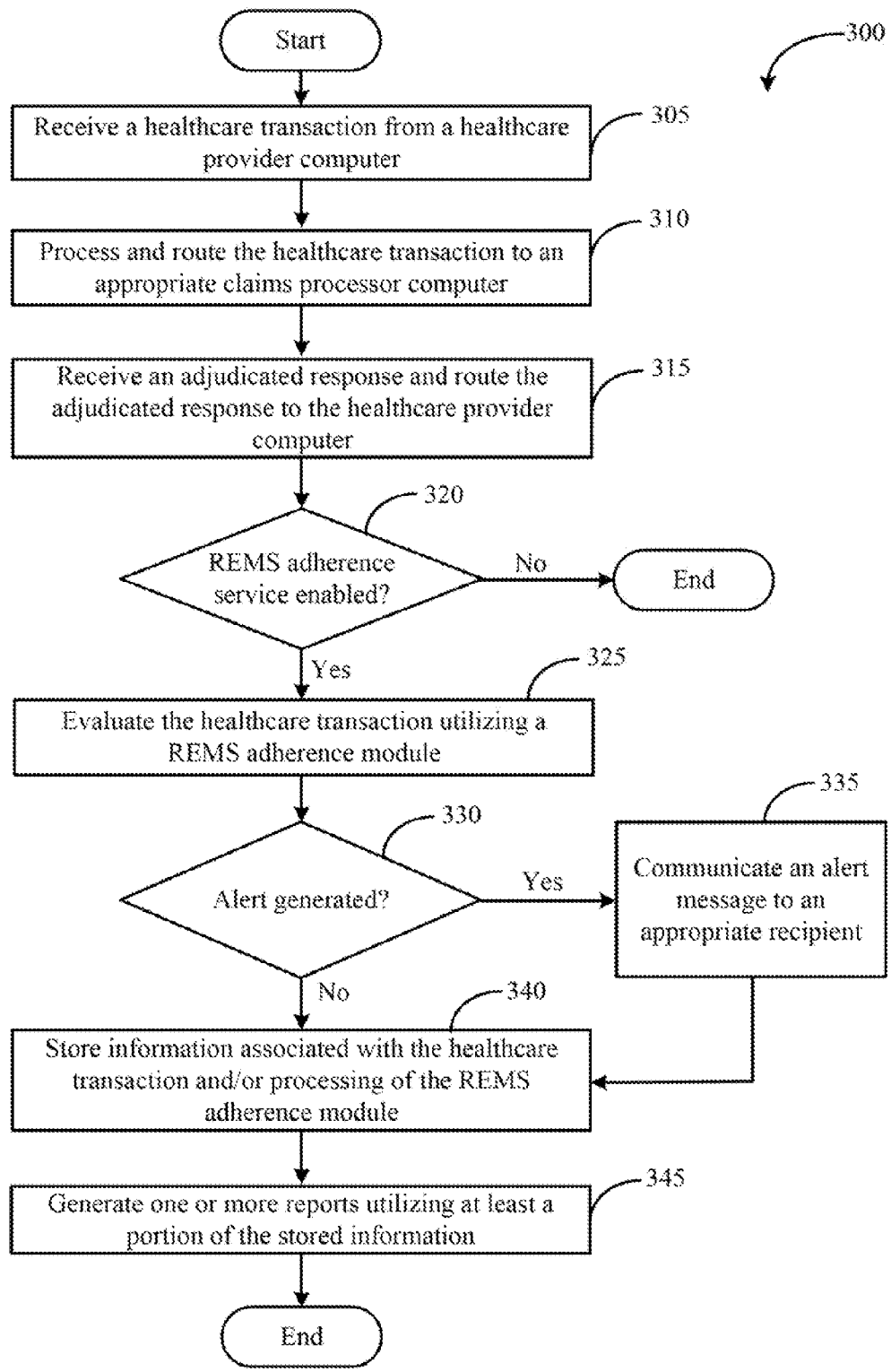
FIG. 3 is a flow diagram of an example method for processing a healthcare transaction, according to an illustrative embodiment of the disclosure.
Figure 4:
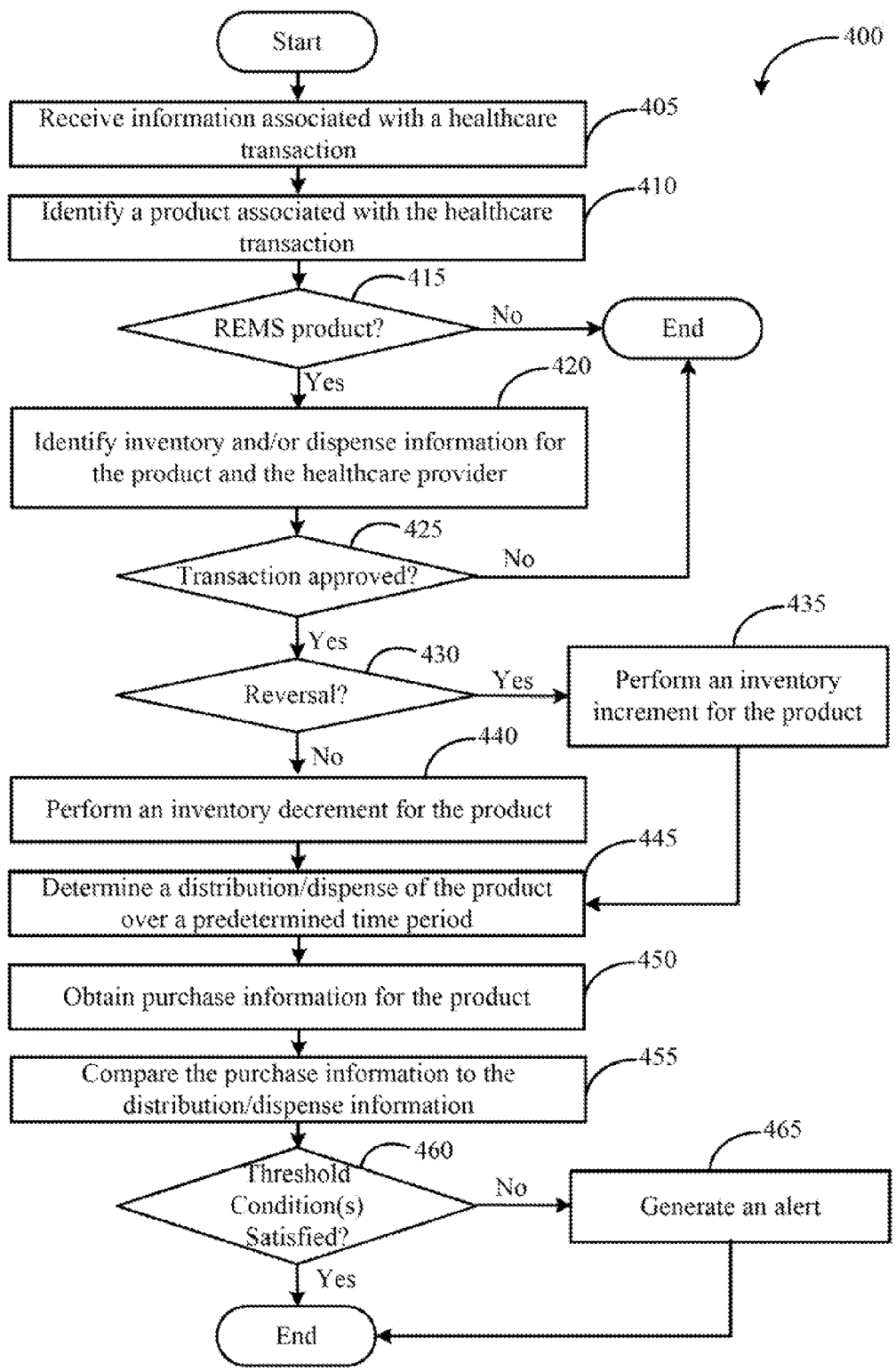
FIG. 4 is a flow diagram of an example method for identifying potential fraud and/or abuse in association with the distribution of a product, according to an illustrative embodiment of the disclosure.

FIG. 4 is a flow diagram of an example method 400 for identifying potential fraud and/or abuse in association with the distribution of a product, according to an illustrative embodiment. The method 400 illustrated in FIG. 4 may be an example implementation of block 325 shown in FIG. 3. As such, the method 400 may be performed by a suitable service provider computer and/or REMS adherence module, such as the service provider computer 104 and/or the REMS adherence module 180 illustrated in FIG. 1. The method 400 may begin at block 405.

At block 405, information associated with a healthcare transaction may be received by the REMS adherence module 180. For example, a copy of the healthcare transaction and/or information extracted from the healthcare transaction may be received. At block 410, a product associated with the healthcare transaction may be identified. For example, an NDC code, other product identifier (e.g., Universal Product Code, etc.), or product name included in the healthcare transaction may be identified. At block 415, a determination may be made as to whether the identified product is a REMS product or a product for which a REMS adherence service should be provided. For example, a determination may be made as to whether the identified product is a controlled substance designated for REMS monitoring. A wide variety of suitable methods and/or techniques may be utilized to determine whether the identified product is a REMS product. For example, product identifying information may be compared to stored information associated with REMS products (e.g., a list of REMS products, etc.), and the product may be identified as a REMS product in the event that a match or correspondence is identified. If it is determined at block 415 that the product is not a REMS product, then operations of the method 400 may end. If, however, it is determined at block 415 that the product is a REMS product, then operations may continue at block 420.

At block 420, a dispense amount and/or inventory information for the product and the healthcare provider may be determined. For example, a stored dispense amount associated with the product and the healthcare provider may be accessed from memory and/or obtained from an external source. In certain embodiments, the stored dispense amount may monitor or track a dispensed amount of the product based upon healthcare transactions submitted by the pharmacy. As desired, the stored dispense amount may be derived from healthcare transactions submitted for any desired historical period of time, such as the last month, the last three months, or some other period of time. As another example, a stored inventory amount may be accessed from memory and/or obtained from an external source. The inventory amount may track and/or estimate an available inventory of the product at the healthcare provider based upon the processing of healthcare transactions. For example, an initial inventory may be determined, and the inventory may be modified based upon processed healthcare transactions. Additionally, as explained in greater detail below with reference to block 450, the inventory may be modified based upon order and/or purchase information.

At block 425, a determination may be made as to whether the healthcare transaction has been approved. For example, a received adjudication response for the healthcare transaction may be evaluated in order to determine whether the underlying healthcare transaction has been approved by a claims processor. If it is determined at block 425 that the healthcare transaction has not been approved, then the method 400 may end. If, however, it is determined at block 425 that the healthcare transaction has been approved, then operations may continue at block 430.

At block 430, a determination may be made as to whether the healthcare transaction is a reversal transaction. In other words, a determination may be made as to whether the healthcare transaction is a healthcare claim transaction associated with a dispense of the product or a reversal transaction intended to reverse a previously processed healthcare claim transaction. If it is determined at block 430 that the healthcare transaction is a reversal transaction, then operations may continue at block 435. At block 435, it may be assumed that an amount of the product associated with the healthcare transaction has not been dispensed. As a result, a dispense amount associated with the product may be decremented by an amount of the product associated with the reversal transaction. For example, if a reversal transaction reverses a previous claim for 30 units of the product, the dispense amount associated with the product may be decremented by 30 units. Alternatively, an inventory amount associated with the product may be incremented by an amount of the product associated with the reversal transaction. Operations may then continue at block 445.

If, however, it is determined at block 430 that the healthcare transaction is not a reversal transaction, then operations may continue at block 440. At block 440, it may be determined that the healthcare transaction is a healthcare claim transaction. Additionally, it may be assumed that an amount of product associated with the healthcare transaction has been dispensed by the healthcare provider to a patient. As a result, a dispense amount associated with the product may be incremented by an amount of the product associated with the healthcare transaction. Alternatively, an inventory amount associated with the product may be decremented by an amount of the product associated with the healthcare transaction. Operations may then continue at block 445.

At block 445, which may be reached from either block 435 or block 440, a dispense or distribution amount for the product by the healthcare provider may be determined over a predetermined period of time, such as a previous month, a previous three-month period, or some other period of time. In certain embodiments, a dispense amount maintained by the REMS adherence module 180 may track a rolling period of received and processed healthcare transactions associated with the product. In this regard, dispensing activity for the product, as reflected by submitted healthcare transactions, may be maintained over a desired time period. In other embodiments, inventory information associated with the desired time period may be evaluated in order to determine a dispense or distribution amount of the product over the desired time period. For example, a current inventory amount for the product may be subtracted from an inventory amount at the beginning of the desired time period to determine a dispense amount of the product. As desired, the monitoring of inventory amounts may be adjusted based upon known purchasing and/or ordering activity. Additionally, in certain embodiments, a dispense amount may be derived from a combination of monitored dispenses and/or inventory information. Indeed, a wide variety of suitable methods and/or techniques may be utilized to determine a dispense amount over a predetermined period of time.

At block 450, order and/or purchase information for the product may be obtained from a wide variety of suitable sources. For example, order and/or purchase information may be obtained from a supplier computer associated with a manufacturer, distributor, and/or supplier of the product. As another example, information may be obtained from the inventory management module 184. A wide variety of different types of order and/or purchase information may be obtained as desired, including but not limited to, invoice data, shipment data, and/or billing data. The purchase information may be indicative of an amount of product that has likely been distributed by the healthcare provider over any desired period of time. For example, the purchase information may be evaluated in order to determine an amount of product supplied or provided to the healthcare provider. Taking stocking and/or inventory considerations into account, an amount of the product that has likely been distributed by the healthcare provider may be estimated.

At block 455, the purchase information (or likely distribution amount) may be compared to the dispense information (i.e., the dispense/distribution information obtained from healthcare transaction monitoring). For example, an amount of the product supplied to the healthcare provider over a period of time may be compared to the claim and/or billing transaction data submitted by the healthcare provider for the product. In this regard, a wide variety of REMS compliance may be evaluated and/or potentially fraudulent situations may be identified.

A wide variety of suitable methods and/or techniques may be utilized to evaluate the purchase information and the dispense information. For example, the results of a comparison may be evaluated utilizing any number of suitable threshold conditions and/or REMS parameters. As one example, a difference between a purchase amount and a determined dispense amount may be compared to one or more threshold conditions. As another example, a deviation (e.g., a standard deviation, etc.) between a purchase amount and a determined dispense amount may be compared to one or more threshold conditions. In this regard, a determination may be made as to whether the healthcare provider is ordering a greater amount of product than the amount of dispensed product indicated in healthcare transaction activity. For example, if a deviation between a determined dispensed amount and an ordered or purchased amount exceeds a threshold, then a potentially fraudulent situation in which a healthcare provider may be dispensing product (e.g., controlled substances) without submitting healthcare transactions may be identified. As another example, a potentially fraudulent situation may be identified if a difference between a managed inventory amount (i.e., an inventory amount managed in conjunction with healthcare transaction activity) and an expected inventory from purchasing information exceeds a predetermined threshold. Indeed, a wide variety of different types of thresholds and/or conditions may be evaluated in order to identify potentially fraudulent activity.

At block 460, a determination may be made as to whether one or more threshold conditions have been satisfied by an evaluation of purchase information and distribution/dispense information. If it is determined at block 460 that the one or more threshold conditions have been satisfied (i.e., no potentially fraudulent activity is identified), then the method 400 may end. If, however, it is determined at block 460 that one or more threshold conditions have not been satisfied, then operations may continue at block 465. At block 465, a potentially fraudulent situation or other situation associated with failure to satisfy REMS conditions may be identified. Additionally, a suitable alert message associated with the potentially fraudulent situation (or other situation) may be generated and communicated to one or more suitable recipients, such as a REMS administrator and/or a healthcare provider back office computer.

The method 400 may end following either block 415, block 425, block 460, or block 465.

The operations described and shown in the methods 300, 400 of FIGS. 3-4 may be carried out or performed in any suitable order as desired in various embodiments of the invention. Additionally, in certain embodiments, at least a portion of the operations may be carried out in parallel. Furthermore, in certain embodiments, less than or more than the operations described in FIGS. 3-4 may be performed.

Accordingly, example embodiments of the disclosure can provide the technical effects of evaluating healthcare transactions to determine dispense and/or inventory amounts for various products distributed by a healthcare provider. Additionally, the determined dispense and/or inventory amounts may be compared to and/or otherwise evaluated in association with ordering and/or purchasing information for the products by the healthcare providers. In this regard, potential fraud and/or potential REMS non-compliance by the healthcare provider may be identified.

Various block and/or flow diagrams of systems, methods, apparatus, and/or computer program products according to example embodiments of the invention are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments of the invention.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flow diagram block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the invention may provide for a computer program product, comprising a computer usable medium having a computer-readable program code or program instructions embodied therein, said computer-readable program code adapted to be executed to implement one or more functions specified in the flow diagram block or blocks. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram block or blocks.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special purpose, hardware-based computer systems that perform the specified functions, elements or steps, or combinations of special purpose hardware and computer instructions.

Many modifications and other embodiments of the invention set forth herein will be apparent having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for identifying Risk Evaluation and Mitigation Strategies (REMS) compliance, the method comprising:
routing, by a service provider system comprising one or more computers, one or more healthcare transactions submitted by a healthcare provider to one or more claims processor computers;
routing, by the service provider system to the healthcare provider, one or more respective adjudicated replies received from the one or more claims processor computers for the one or more healthcare transactions;
determining, by the service provider system based at least in part upon information included in the routed healthcare claim transactions and adjudicated replies, an amount of a product dispensed by the healthcare provider;
comparing, by the service provider system, the determined dispensed amount to a purchased amount of the product; and determining, by the service provider system based at least in part upon the comparison, whether a REMS condition associated with the product is satisfied.

2. The method of claim 1, wherein determining whether a REMS condition is satisfied comprises determining whether fraudulent distribution of the product is potentially occurring.

3. The method of claim 1, wherein determining whether a REMS condition is satisfied comprises determining whether a deviation between the purchased amount and the dispensed amount satisfies a threshold condition.

4. The method of claim 1, further comprising:
generating, by the service provider system, a REMS alert message associated with the product; and
communicating, by the service provider system, the generated REMS alert message to a designated recipient.

5. The method of claim 1, wherein one of the one or more healthcare transactions comprise (i) a healthcare claim transaction or (ii) a healthcare claim reversal transaction, and wherein determining an amount of the product dispensed by the healthcare provider comprises:
determining, by the service provider system based at least in part upon evaluating an adjudicated reply associated with the healthcare transaction, that the healthcare claim transaction has been approved; and
determining, by the service provider system based at least in part upon the approval determination, the dispensed amount.

6. The method of claim 1, further comprising:
determining, by the service provider system, that the product is a controlled substance.

7. The method of claim 1, further comprising:
obtaining, by the service provider system, purchasing information for the product; and
determining, by the service provider system based upon at least a portion of the obtained purchasing information, the purchased amount.

8. The method of claim 7, wherein obtaining purchasing information comprises obtaining at least one of (i) invoices, (ii) shipment information, or (iii) ordering information.

9. The method of claim 7, wherein obtaining purchasing information comprises obtaining purchasing information from at least one of (i) a supplier of the product, (ii) a distributor of the product, or (iii) a manufacturer of the product.

10. The method of claim 1, further comprising:
determining, by the service provider system, an inventory amount associated with the product; and
communicating, by the service provider system based at least in part upon the inventory amount, a message associated with the purchase of additional product.

11. A system for Risk Evaluation and Mitigation Strategies (REMS) compliance, the system comprising:
at least one memory configured to store computer-executable instructions; and
at least one processor configured to access the at least one memory and execute the computer-executable instructions to:
direct the routing of one or more healthcare transactions submitted by a healthcare provider to one or more claims processor computers;
direct the routing, to the healthcare provider, of one or more respective adjudicated replies received from the one or more claims processor computers for the one or more healthcare transactions;
determine, based at least in part upon information included in the routed healthcare claim transactions and adjudicated replies, an amount of a product dispensed by the healthcare provider;
compare the determined dispensed amount to a purchased amount of the product; and
determine, based at least in part upon the comparison, whether a REMS condition associated with the product is satisfied.

12. The system of claim 11, wherein the REMS condition comprises a condition associated with potential fraudulent distribution of the product.

13. The system of claim 11, wherein the at least one processor is configured to determine whether the REMS condition is satisfied by executing the computer-executable instructions to determine whether a deviation between the purchased amount and the dispensed amount satisfies a threshold condition.

14. The system of claim 11, wherein the at least one processor is further configured to execute the computer-executable instructions to:
generate a REMS alert message associated with the product; and
direct communication of the generated REMS alert message to a designated recipient.

15. The system of claim 11, wherein one of the one or more healthcare transactions comprise (i) a healthcare claim transaction or (ii) a healthcare claim reversal transaction, and wherein the at least one processor is configured to determine an amount of the product dispensed by the healthcare provider by executing the computer-executable instructions to:
determine, based at least in part upon evaluating an adjudicated reply associated with the healthcare transaction, that the healthcare claim transaction has been approved; and
determine, based at least in part upon the approval determination, the dispensed amount.

16. The system of claim 11, wherein the at least one processor is further configured to execute the computer-executable instructions to:
determine that the product is a controlled substance.

17. The system of claim 11, wherein the at least one processor is further configured to execute the computer-executable instructions to:
obtain purchasing information for the product; and
determine, based upon at least a portion of the obtained purchasing information, the purchased amount.

18. The system of claim 17, wherein the obtained purchasing information comprises at least one of (i) invoices, (ii) shipment information, or (iii) ordering information.

19. The system of claim 17, wherein the purchasing information is obtained from at least one of (i) a supplier of the product, (ii) a distributor of the product, or (iii) a manufacturer of the product.

20. The system of claim 11, wherein the at least one processor is further configured to execute the computer-executable instructions to:
determine an inventory amount associated with the product; and
direct communication, based at least in part upon the inventory amount, of a message associated with the purchase of additional product.

* * * * *